United States Patent [19]
Ellison et al.
[11] 4,129,577
[45] Dec. 12, 1978

[54] DERIVATIVE OF T-2 TOXIN AND ANGUIDINE

[75] Inventors: Robert A. Ellison, Madison, Wis.; Frank N. Kotsonis, Kansas City, Mo.

[73] Assignee: Wisconsin Alumni Research Foundation, Madison, Wis.

[21] Appl. No.: 826,067

[22] Filed: Aug. 19, 1977

Related U.S. Application Data

[63] Continuation of Ser. No. 646,647, Jan. 5, 1976, abandoned.

[51] Int. Cl.[2] .................... C07C 311/02; A61K 31/35
[52] U.S. Cl. .................................. 260/345.2; 424/283
[58] Field of Search ...................................... 260/345.2

[56] References Cited

U.S. PATENT DOCUMENTS 3,428,652 2/1969 Sigg et al. ........................ 260/345.2

FOREIGN PATENT DOCUMENTS 1372122 9/1964 France ................................ 260/345.2

OTHER PUBLICATIONS

Tasuno, et al., Chem. Abstract, 82, 165,915h (1975).
Bamburg, Clinical Toxicology, 5, 495 (1972), abstracted in Chem. Abstract, 78, 80396g (1973).

*Primary Examiner*—Nicky Chan
*Attorney, Agent, or Firm*—McDougall, Hersh & Scott

[57] ABSTRACT

3-acyl and 3-alkyl trichothecene derivatives having the general formula

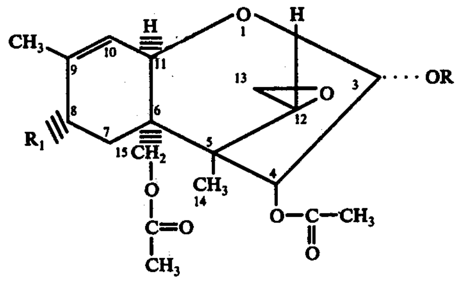

in which $R_1$ is hydrogen or

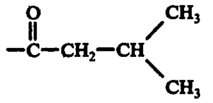

and R is an acyl group

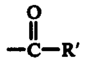

in which R′ is a branched or straight-chained aliphatic, cycloaliphatic or aromatic group having from 2 to 12 carbon atoms or a carbamate group

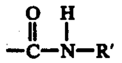

in which R′ has the same meaning as above or an alkyl group, either branched or straight-chained, or an aromatic group having from 1 to 12 carbon atoms.

3 Claims, No Drawings

DERIVATIVE OF T-2 TOXIN AND ANGUIDINE

This is a continuation of Ser. No. 646,647, filed on Jan. 5, 1976, now abandoned.

The invention described herein was made in the course of work under a grant or award from the Department of Health, Education, and Welfare.

This invention relates to 3-acyl and 3-alky trichothecene derivatives and to the method for preparation of such 3-acyl and 3-alkyl derivatives having the general formula

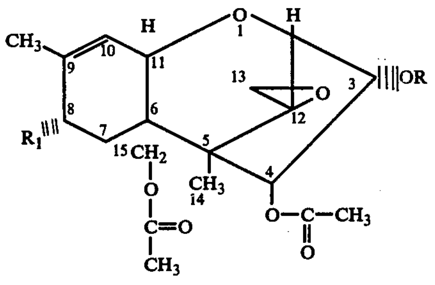

When R is hydrogen and $R_1$ is hydrogen, the compound is known as 3-hydroxy-4,15-diacetoxy-12,13-epoxy-$\Delta^9$-trichothecene, and is generally referred to as diacetoxyscirpenol or anguidine. When R is hydrogen and $R_1$ is

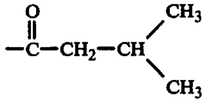

the compound is identified as 3-hydroxy-4,15-diacetoxy-8-(3-methyl butyryloxy)-12,13-epoxy-$\Delta^9$-trichothecene, or more generally referred to as T-2 toxin.

Both anguidine and T-2 toxin are produced naturally by several species of fungi of the genus *Fusarium* on such food products as corn or grain. Both of these compounds are very toxic and find use as cytotoxic agents which destroy cell cultures. A characteristic feature of this family of sesquiterpenes is the pronounced cytotoxicity of most of its members. In tests with pigeons, both T-2 toxin and anguidine also cause vomiting.

The oral $LD_{50}$ (dose at which 50% of the pigeons are killed) is 2.7 mg/kg and the oral $TD_{50}$ (level which makes 50% of the pigeons vomit) is 0.75 mg/kg.

It has been found that acylation to substitute an acyl group for the hydrogen at R on the $C_3$ position greatly increases the activity of the derivative while making it much less toxic to animals. For example, when R is

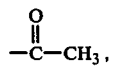, hereinafter referred to as AT-2 toxin, the oral $LD_{50}$ with pigeons becomes at least 18 mg/kg, or less than 1/6 the toxicity of T-2 toxin, while vomiting was virtually completely eliminated. In mice, wherein the compounds were tested by injection into the intraperitoneal cavity as compared to oral administration with pigeons, the difference in toxicity was not as great, although substantial, in that the AT-2 toxin was less than ½ as toxic as T-2 toxin.

In protocol 1.6 of the NCI anti-cancer screen, (a KB cell culture assay — a human epidermal carcinoma), AT-2 toxin was about 5,000 times more active than T-2 toxin.

It has been found further that the compound is more stable to hydrolysis and that the toxicity of the compound is further desirably reduced when the acyl group applied to the $C_3$ position contains at least 3 carbon atoms, but not more than 12 carbon atoms in the aliphatic or cycloaliphatic group, branched or straight chained, and when the R group preferably contains from 3 to 5 carbon atoms.

The following illustrates the growth of KB cells in nutrient solution (NCI protocol 1.6) affected by compounds which, except for acetoxy, are representative of the practice of this invention:

| R | Activity in μg/ml* | Common name |
|---|---|---|
| a) 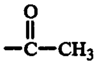 | $10^{-8}$ | AT-2 |
| b) 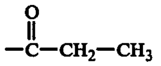 | $10^{-8}$ | PT-2 |
| c) 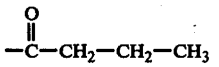 | $10^{-9}$ | BT-2 |
| d) 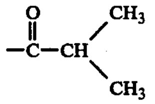 | $10^{-8}$ | iBT-2 |
| e) 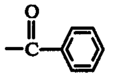 | 10 | BzT-2 |
| f) $-CH_3$ | $10^{-2}$ | MT-2 |

*$ED_{50}$ = concentration causing 50% inhibition of growth

It is believed that the larger acyl groups are hydrolyzed more slowly which has the effect of preventing or slowing the production of the more toxic T-2 toxin and further that the larger acyl groups also render the compound intrinsically less toxic. The alky derivatives, although less cytotoxic, completely prevent hydrolysis. Thus, an important concept of this invention resides in the acyl and alkyl derivatives of T-2 toxin and anguidine wherein the acyl group has from 2 to 12 carbon atoms and preferably 3 to 5 carbon atoms and the alkyl group has from 1 to 12 carbon atoms.

Included also within the scope of this invention are the urethane derivatives represented by the group

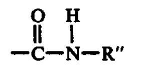

wherein R″ is an alkyl or cycloalkyl group (branched or straight chained) containing from 1 to 11 carbon atoms, as previously defined, including ethyl, propyl, isopropyl, butyl, isobutyl, cyclopropyl, cyclopentyl, and the like. The derivatives are characterized by greater water solubility which enables use by oral administration instead of by injection into the intraperitoneal cavity, but they are less active as cytotoxic agents than the described acyl derivatives.

The derivatives of this invention are prepared using T-2 toxin or anguidine as the starting material, both of which are available from fermentation using a number of strains of the fungal genus *Fusarium*. For the preparation of the acyl derivatives, T-2 toxin, for example, is reacted with

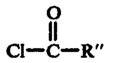

or the anhydride

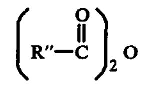

in which R" signifies a straight or branched chain aliphatic, cycloaliphatic or aromatic group having from 1 to 11 carbon atoms. For the preparation of the carbamate (the urethane derivative), T-2 toxin is reacted with O=C=N—R" wherein R" has the same meaning as above. The alkyl ethers are prepared by reacting T-2 toxin with I-R" where R" has the same meaning as above and from 1 to 12 carbon atoms.

The following are specific examples of the preparation of derivatives of this invention:

EXAMPLE 1

Preparation of BT-2 in which

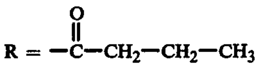

A mixture of T-2 toxin (200 mg, 0.428 m mol), butyric anhydride (4.0 g, 25 m mol) and pyridine (5 drops) is stirred overnight at room temperature under anhydrous conditions. The excess anhydride and pyridine are removed by high vacuum distillation (< 1mm, 75°). The oily residue is dissolved in ether and washed once with 5% aqueous sodium bicarbonate followed by two washings with water. The ether layer is separated, dried over anhydrous sodium sulfate and evaporated to yield 3-n-butyryloxy-T-2 toxin as a white solid (187mg). This may be further purified by column chromatography (silica gel, ethyl acetate — Skellysolve B, 5.7:1).

EXAMPLE 2

Instead of butyric anhydride, others of the $C_3$ to $C_{12}$ aliphatic or cycloaliphatic, branched or stright chained anhydrides are substituted in equimolecular amounts for butyric anhydride to produce the corresponding derivatives.

EXAMPLE 3

Preparation of iBT-2 in which

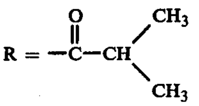

To a solution of T-2 toxin (25 mg, 0.054 m mol) in ether (1 ml) was added pyridine (5 drops) and isobutyryl chloride (5 drops). The reaction mixture is stirred overnight at room temperature under anhydrous conditions. The mixture is then diluted with chloroform (10 ml) and washed sucessively with ice-cold water (10 ml), cold 5% aqueous sodium bicarbonate and then cold water (10 ml). The organic layer is separated, dried over anhydrous sodium sulfate and evaporated to afford 3-isobutyryloxy T-2 toxin as a white solid. This compound may be further purified by column chromatography as in Example 1.

EXAMPLE 4

The isobutyryl chloride of Example 3 is replaced by equimolecular amounts of

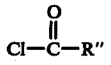

in which R" is a branched or straight chained alkyl, cycloalkyl or aromatic group having from 2 to 11 carbon atoms to yield the corresponding 3-acyl derivative of T-2 toxin, or the corresponding 3-acyl derivative of anguidine, when anguidine is substituted for the T-2 toxin, in equimolecular amounts, in Example 3.

EXAMPLE 5

Preparation of T-2 toxin-3-(N-isopropyl) carbamate

A mixture of 20 mg T-2 toxin (0.044 mmol) and 1 ml isopropyl isocyanate is refluxed in a dry, round bottomed flask fitted with a dry ice condenser. After 24 hours, the excess isocyanate was removed by distillation under high vacuum. The residue was dissolved in chloroform (10 mg) and extracted once with 5% aqueous sodium bicarbonate and then with 10 ml of water. The organic layer was dried with sodium sulphate and evaporated in vacuo to yield 38 mg of a white solid identified as T-2 toxin-3-(N-isopropyl) carbamate.

EXAMPLE 6

The isopropyl isocyanate in Example 4 is replaced with equimolecular amounts of others of the R" isocyanates described in which the R" group is a $C_1$ to $C_{11}$ branched or straight chained aliphatic or cycloaliphatic group, to produce the corresponding derivatives.

EXAMPLE 7

Preparation of MT-2 ($R = CH_3$)

A solution of T-2 toxin (40 mg, 0.088 mmol) in dry tetrahydrofuran (5 ml) was slowly added to a suspension of sodium hydride (2.11 mg, 0.088 mmol) in dry tetrahydrofuran (10 ml). After 15 minutes, iodomethane (2 drops) was added and the mixture stirred at room temperature under a dry atmosphere. After 3 hours the reaction was diluted with ether (15 ml) and washed three times with cold water (10 ml). The ether layer was separated, dried over anhydrous sodium sulphate and evaporated to yield a yellow residue (35 mg). Purification using preparative thin layer chromatography (silica gel plates, 2 mm; ethyl acetate — Skelly B, 5.7:1) yielded the methyl ether of T-2 toxin (8 mg) as a white solid.

EXAMPLE 8

This example is the same as Example 7 except that iodoethane, iodopropane, iodobutane, benzyl iodide; iodoisobutane or other branched or straight chained $C_2$-$C_{12}$ alkanes are substituted in equal molecular amounts for iodomethane in Example 7 to produce the corresponding ether derivatives.

EXAMPLE 9

When the T-2 toxin in Example 5 is replaced with anguidine, the corresponding 3-acyl and 3-alkyl derivatives are produced.

We claim:

1. A compound having the general formula

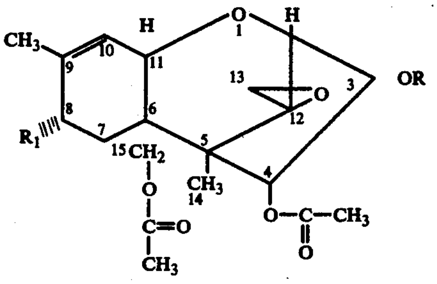

in which $R_1$ is

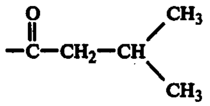

and R is an alkanoate having the general formula

in which R" is an alkyl group having from 1 to 11 carbon atoms.

2. The compound as claimed in claim 1 in which the R" group has from 2 to 5 carbon atoms.

3. The compound as claimed in claim 1 in which the R group is selected from the group consisting of

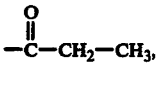,
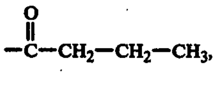,
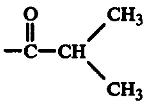

* * * * *